United States Patent
Laugharn, Jr. et al.

(10) Patent No.: US 11,092,521 B2
(45) Date of Patent: Aug. 17, 2021

(54) METHOD AND SYSTEM FOR ACOUSTICALLY TREATING MATERIAL

(71) Applicant: Covaris, Inc., Woburn, MA (US)

(72) Inventors: James A. Laugharn, Jr., Winchester, MA (US); Xiaoyin He, Waltham, MA (US)

(73) Assignee: Covaris, Inc., Woburn, MA (US)

( * ) Notice: Subject to any disclaimer, the term of this patent is extended or adjusted under 35 U.S.C. 154(b) by 620 days.

(21) Appl. No.: 14/463,730

(22) Filed: Aug. 20, 2014

(65) Prior Publication Data
US 2015/0056715 A1    Feb. 26, 2015

Related U.S. Application Data

(60) Provisional application No. 61/868,213, filed on Aug. 21, 2013.

(51) Int. Cl.
| | | |
|---|---|---|
| *G01N 1/00* | (2006.01) | |
| *G01N 1/40* | (2006.01) | |
| *C12M 1/42* | (2006.01) | |

(52) U.S. Cl.
CPC ........... *G01N 1/4044* (2013.01); *C12M 35/04* (2013.01); *G01N 2001/4094* (2013.01); *Y10T 436/25125* (2015.01)

(58) Field of Classification Search
CPC .... G01N 29/27; G01N 29/265; G01N 29/275; G01N 29/28; G01N 29/2493; G01N 29/225
See application file for complete search history.

(56) References Cited

U.S. PATENT DOCUMENTS

| | | | |
|---|---|---|---|
| 6,688,178 B1 * | 2/2004 | Schmidt | G01N 29/2493 73/639 |
| 7,521,023 B2 | 4/2009 | Laugharn | |
| 2007/0053795 A1 * | 3/2007 | Laugharn, Jr. | B01F 11/0283 73/644 |
| 2009/0249877 A1 * | 10/2009 | Vivek | G01N 29/221 73/579 |

* cited by examiner

*Primary Examiner* — Christopher Adam Hixson
(74) *Attorney, Agent, or Firm* — Wolf, Greenfield & Sacks, P.C.

(57) ABSTRACT

Methods and systems for acoustically treating material using an acoustic energy system having a movable outer surface that contacts a sample holder. The outer surface may be cylindrical and rotate about a central axis, e.g., so that a sample holder may be driven to move by the outer surface. Acoustic energy may be emitted from within the outer surface to a treatment area outside of, and near, the outer surface. Thus, a sample holder in contact with the outer surface may have a sample exposed to acoustic energy while rotation of the outer surface may move the sample holder relative to treatment area. One or more additional rollers or other components may bias the sample holder into contact with the outer surface, e.g., so the sample holder is squeezed between the outer surface and a roller or other biasing component.

15 Claims, 3 Drawing Sheets

METHOD AND SYSTEM FOR ACOUSTICALLY TREATING MATERIAL

CROSS REFERENCE TO RELATED APPLICATION

This application claims the benefit of U.S. Provisional Application No. 61/868,213, filed Aug. 21, 2013, which is hereby incorporated by reference in its entirety.

BACKGROUND

1. Field of Invention

The present invention generally relates to the field of controlled sonic energy emitting devices for treating material.

2. Related Art

Ultrasonics have been utilized for many years for a variety of diagnostic, therapeutic, and research purposes. The acoustic physics of ultrasonics is well understood; however, the biophysical, chemical, and mechanical effects are generally only empirically understood. Some uses of sonic or acoustic energy in materials processing include "sonication," an unrefined process of mechanical disruption involving the direct immersion of an unfocused ultrasound source emitting energy in the kilohertz ("kHz") range into a fluid suspension of the material being treated. Accordingly, the sonic energy often does not reach a target in an effective dose because the energy is scattered, absorbed, and/or not properly aligned with the target. Sonication has also hit limits on effectiveness when applied to higher sample volumes or continuous process streams. There are also specific clinical examples of the utilization of therapeutic ultrasound (e.g., lithotripsy) and of diagnostic ultrasound (e.g., fetal imaging). However, ultrasonics have heretofore not been controlled to provide an automated, broad range, precise materials processing or reaction control mechanism. In U.S. Pat. No. 7,521,023 and others, the use of 'focused acoustical energy' is described to overcome some of the limitations of traditional 'sonication.' Focusing the acoustical energy has many advantages, and can be effective at processing high sample volumes or continuous process streams.

SUMMARY OF INVENTION

The present invention relates to systems and methods for treating sample material with focused acoustical energy. The desired result of acoustic treatment, which may be achieved or enhanced by use of ultrasonic wavetrains, can be without limitation, heating the sample, cooling the sample, fluidizing the sample, micronizing the sample, mixing the sample, stirring the sample, disrupting the sample, permeabilizing a component of the sample, forming a nanoemulsion or nano formulation, enhancing a reaction in the sample, solubilizing, sterilizing the sample, lysing, extracting, comminuting, catalyzing, and selectively degrading at least a portion of a sample. Sonic waves may also enhance filtration, fluid flow in conduits, and fluidization of suspensions. Processes of the invention may be synthetic, analytic, or simply facilitative of other processes, such as stirring.

For example, altering the permeability or accessibility of a material in a controlled manner can allow for manipulation of the material while preserving the viability and/or to biological activity of the material. In another example, mixing materials or modulating transport of a component into or out of materials, in a reproducible, uniform, and automated manner, can be beneficial. According to one embodiment of the system, sample processing control includes a feedback loop for regulating at least one of sonic energy location, pulse pattern, pulse intensity, duration, and absorbed dose of the ultrasound to achieve the desired result of acoustic treatment. In one embodiment, the ultrasonic energy is in the sub-megahertz to megahertz (MHz) frequency range, in contrast to classical sonic processing which typically employs ultrasonic energy in the kilohertz (kHz) frequency range.

In one aspect of the invention, a system for treating a material with acoustic energy includes a coupling medium container that is closed, defines an internal volume, and has an outer surface arranged to rotate about an axis. For example, the coupling medium container may be formed as a cylinder with an internal space and an outer surface arranged to rotate about a longitudinal axis of the cylinder. An acoustic energy source may be arranged to emit acoustic energy into the internal volume, e.g., an acoustic transducer may be arranged in the internal volume of the coupling medium container so that acoustic energy is emitted into the internal volume. A coupling medium, such as water, an oil, a gel, or other material, may be located in the internal volume of the coupling medium container and be arranged to transmit acoustic energy from the acoustic energy source to a treatment area outside of the coupling medium container and near the outer surface. For example, the energy source may be arranged to emit acoustic energy generally radially outwardly from an interior space of a cylindrical coupling medium container. The coupling medium may transmit the acoustic energy from the energy source toward the outer surface of the coupling medium container. A sample holder may be positionable in contact with the outer surface of the coupling medium container, e.g., so that the sample holder may receive acoustic energy from the outer surface, and the outer surface may be rotatable with movement of the sample holder relative to the treatment area. For example, a sample holder may be moved along a straight line while in contact with the coupling medium container. The outer surface of the container may rotate and maintain contact with the sample holder as the sample holder moves along the straight path.

In some embodiments, the outer surface of the coupling medium container may be cylindrical and the axis about which the outer surface may rotate passes through a center longitudinal axis of the cylindrical outer surface. Thus, as noted above, the outer surface may be rotatable with linear movement of the sample holder relative to the treatment area, e.g., the outer surface may be rotatable with movement of the sample holder along a direction parallel to a tangent of the outer surface.

The coupling medium may be liquid, e.g., the liquid may completely fill the coupling medium container and a transducer of the acoustic energy source may be immersed or otherwise in contact with the liquid. The acoustic energy source may be arranged to emit acoustic energy having a frequency of about 100 kHz to 100 MHz that creates a focal zone at the treatment area. That is, acoustic energy may be transmitted through the coupling medium and a portion of the coupling medium container to form a focal zone at a treatment area at which a sample (held in a sample holder) is positioned. In some embodiments, a heat exchanger may be arranged to exchange heat with the coupling medium, e.g., to remove heat from the coupling medium that is generated by the acoustic energy source.

In some embodiments, a roller may be positioned above the treatment area and arranged to rotate about a roller axis so that the roller can contact a sample holder positioned between the coupling medium container and the roller. In this way, the sample holder can be urged into contact with the coupling medium container by the roller, helping to maintain proper acoustic energy transmission to the sample holder. In some arrangements, the roller and the outer surface are rotatable to move a sample holder relative to the treatment area. For example, a sample holder may be engaged between the roller and the coupling medium container, and the roller (or the container, or both) may be rotated to feed the sample holder through a treatment area. The sample holder may have a plate shape (e.g., as a multi-well plate), a tube shape, or other arrangements, such as one that conforms to the outer surface of the coupling medium container or is compliant. The outer surface of the coupling medium container may include a resilient material to contact the sample holder, e.g., to help maintain contact between the outer surface and the sample holder so acoustic energy is properly transmitted.

In another aspect of the invention, a method for treating a sample with acoustic energy includes emitting acoustic energy into a coupling medium located in a coupling medium container that is closed and defines an internal volume. The acoustic energy may be transmitted by the coupling medium toward a treatment area outside of the coupling medium container. A sample holder may be positioned in contact with an outer surface of the coupling medium container at the treatment area so that a sample held by the sample holder is to exposed to the acoustic energy. The sample holder may be moved relative to the treatment area, and the outer surface of the coupling medium container may be rotated with movement of the sample holder relative to the treatment area.

As mentioned above, in some embodiments moving the sample holder may include moving the sample holder in response to rotation of the outer surface of the coupling medium container, e.g., by driving rotation of the outer surface of the coupling medium container using a motor. The outer surface of the coupling medium container may be cylindrical and may be rotated about an axis that passes through a center longitudinal axis of the cylindrical outer surface. Moving of the sample holder relative to the treatment area may include moving the holder along a linear path relative to the treatment area, e.g., where the linear path is parallel to a tangent of the outer surface. A roller may be positioned above the treatment area, arranged to rotate about a roller axis, and arranged to urge the sample holder into contact with the coupling medium container. For example, the sample holder may be squeezed between the roller and the outer surface of the coupling medium container, and may move along a path when the roller and/or the outer surface rotate.

In some embodiments, aspects of the invention allow ultrasonic energy to be applied to enclosed or encapsulated "lab-on-a-chip" or cartridge systems. Ultrasonic energy may be applied through the walls, or special windows, of these devices; and the devices may be processed through the apparatus as described, through rotation of the coupling medium container and roller. This allows acoustic energy to be used for different processes in different positions on the cartridge—for example, cell lysis and nucleic acid extraction in one area; enhancement of binding and reduction of non-specific binding in another area—and obviates the inclusion of piezoelectric transducers in the disposable (e.g., well plate or other sample holder), greatly decreasing cost while improving performance.

These and other aspects of the invention will be understood from the following description and claims.

BRIEF DESCRIPTION OF THE DRAWINGS

Illustrative embodiments of the invention are more particularly described in the following detailed description, taken in conjunction with the accompanying drawings. In the drawings, like reference characters generally refer to the same parts throughout the different views.

DETAILED DESCRIPTION

"Sonic energy" as used herein is intended to encompass such terms as acoustic energy, acoustic waves, acoustic pulses, ultrasonic energy, ultrasonic waves, ultrasound, shock waves, sound energy, sound waves, sonic pulses, pulses, waves, or any other grammatical form of these terms, as well as any other type of energy that has similar characteristics to sonic energy. "Focal zone" or "focal point" as used herein means an area where sonic energy converges and/or impinges on a target, although that area of convergence is not necessarily a single focused point, but may include a volume of varying size and shape. As used herein, the terms "treatment area" or "processing zone" means a vessel or region where the sonic energy converges, and the sample material is present for treatment. As used herein, "nonlinear acoustics" can mean lack of proportionality between input and output. For example, as the amplitude applied to an acoustic transducer increases, the sinusoidal output generally loses proportionality along the wave propagation such that eventually the peak positive pressure increases at a higher rate than the peak negative pressure. Also, due to the nonlinearity of the water or other coupling medium properties, the nonlinearity (distortion) of the waveform becomes more dramatic at high acoustic energy intensities, and in a converging acoustic field, the waves become more disturbed as the intensity increases toward the focal point. As used herein, "acoustic streaming" can mean generation of averaged fluid flow over time by acoustic waves. The effect can be non-linear because of nonlinear wave propagations. Bulk fluid flow of a liquid in the direction of the sound field can be created as a result of momentum absorbed from the acoustic field and the velocity of the fluid flow can be significantly increased at high acoustic intensity. As used herein, "acoustic micro-streaming" can mean time-independent circulation that occurs only in a small region of the fluid around a source or obstacle, for example, an acoustically driven bubble in a sound field. As used herein, "acoustic absorption" can refer to a characteristic of a material relating to the material's ability to convert acoustic energy into thermal energy. As used herein, "acoustic impedance" can mean a ratio of sound pressure on a surface to sound flux through the surface, the ratio having a reactance and a resistance component. As used herein, "acoustic scattering" can mean irregular and multi-directional reflection and diffraction of sound waves produced by multiple reflecting surfaces, the dimensions of which are smaller or comparable to the wavelength, or by certain discontinuities in the medium through which the wave is propagated.

Apparatus and Methods for Ultrasonic Treatment

Figure 1:
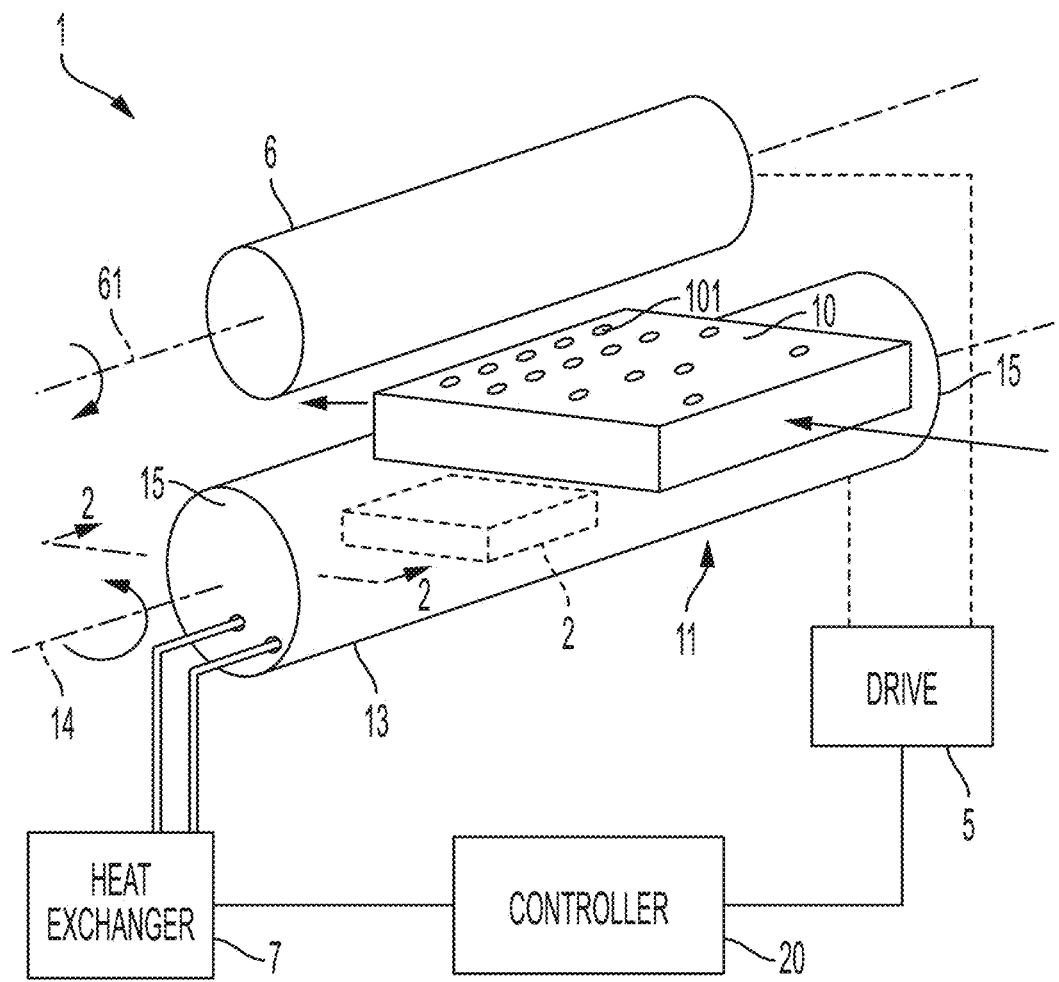
FIG. 1 is a perspective view of an acoustic treatment system in an illustrative embodiment.
Figure 2:
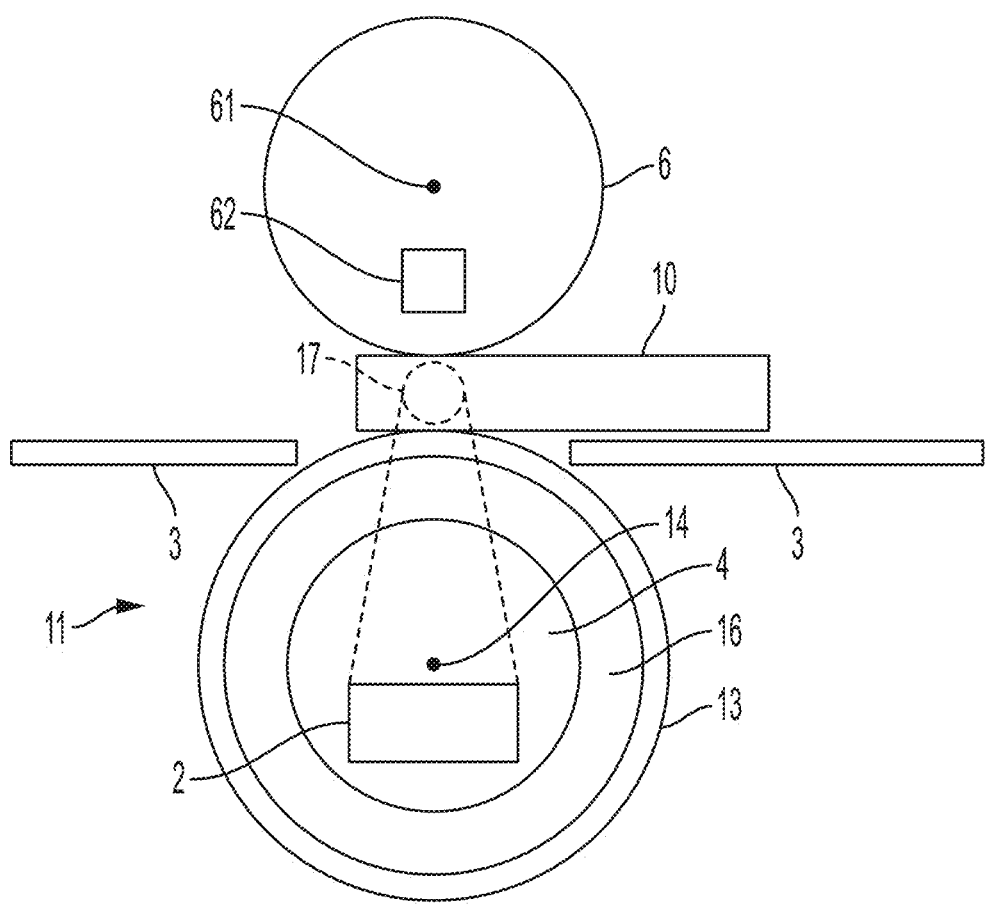
FIG. 2 is a cross sectional side view of the FIG. 1 embodiment.

FIGS. 1 and 2 depict one embodiment of an acoustic treatment system 1 that uses focused acoustic energy to treat a sample held by a sample holder 10. In this embodiment, the sample holder 10 has a plate-type shape and configuration, e.g., the sample holder 10 may be a multi-well plate having 384 or more (or fewer) wells 101, each of which holds a sample. However, the sample holder 10 may take other forms, such as a sample tube or other vessel of any suitable size, shape and/or volume. Thus, the sample holder 10 need not hold multiple samples as in this embodiment, but instead may hold a single sample in a single volume of any suitable size and/or shape. The sample holder 10 may be sealed closed, e.g., the multi-well plate may have a sealing film arranged over the wells 101, or may be open. The sample(s) may include any suitable material intended for acoustic treatment, such as water and/or other liquid combined with a solid or other material (whether in solution or not), such as tissue, DNA or other genomic material, etc. In short, the sample(s) held by the sample holder 10 may be any suitable material or combination of materials to be treated with acoustic energy. In some embodiments, the system 1 may be particularly well suited for enhancing binding reactions in the sample(s), e.g., by enhancing enzyme activity.

In accordance with an aspect of the invention, acoustic energy generated by an acoustic energy source 2 located inside of a coupling medium container 11 passes through the container to a treatment area located outside of and near an outer surface 13 of the container. Thus, sample material held by a sample holder 10, which is positioned in contact with the outer surface 13 of the container 11 near the treatment area, may be exposed to acoustic energy at the treatment area without contacting the coupling medium 4. This in contrast to systems like that described in U.S. Pat. No. 7,521,023, in which the sample holder contacts a liquid coupling medium used to transmit acoustic energy to the sample holder. That is, some prior systems required that a sample holder be at least partially immersed in or in contact with a liquid coupling medium to suitably receive acoustic energy at the sample. However, in accordance with an aspect of the invention, a sample holder and associated sample(s) may receive acoustic energy directly from a coupling medium and coupling medium container without contacting the coupling medium. As a result, the coupling medium may be sealed inside of the coupling medium container 11, avoiding contact of the coupling medium 4 with an outside environment. This approach may help reduce contamination of the coupling medium (which can affect its acoustic energy transmission characteristics) and contamination of the sample (the potential leaking of the vessel) as well as make acoustic treatment simpler, e.g., by eliminating any need to remove residual coupling medium from the sample holder after treatment.

In this illustrative embodiment, the acoustic energy source 2, which may include a piezoelectric transducer or other suitable component(s), may be suspended or otherwise positioned in contact with a liquid coupling medium 4 inside of the coupling medium container 11 and arranged to emit acoustic energy to a treatment zone outside of the container 11. Together with the coupling medium container 11, the coupling medium 4, which may be an oil or water-based compound, may assist in suitably transmitting acoustic energy from the acoustic energy source 2 to the treatment area outside of the container 11. The acoustic energy may be focused by the acoustic energy source 2 (and/or other components of the system 1) so as to form a focal zone 17 (see FIG. 2) at the treatment area, or the acoustic energy may be unfocused. In this illustrative embodiment, a focal zone 17 of acoustic energy is formed at the treatment area, and the coupling medium container 11 (including an interface between the container 11 and the coupling medium 4) may have a lensing effect, or not, on the acoustic energy to assist in the formation of the focal zone 17. In addition, or alternately, the acoustic energy source 2 may be physically arranged (e.g., with a curved emission surface) and/or controlled (e.g., using a phased array approach) to generate a desired focal zone 17 of acoustic energy. As is discussed in more detail below, the acoustic treatment system 1 may include a controller 20 (e.g., including a suitably programmed general purpose computer or other data processing device) that receives control information (e.g., from one or more sensors, user input devices, etc.) and correspondingly controls operation of the acoustic energy source 2 and/or other system components.

By positioning the sample holder 10 in contact with the outer surface 13 of the container 11, a transmission path for acoustic energy from the source 2 to the sample(s) may be controlled, e.g., so that acoustic energy of a desired power, frequency, etc., is applied to the sample. That is, the coupling medium 4 and container 11 may be arranged to minimize or otherwise carefully control scattering or other effects on the acoustic energy so that acoustic energy having desired characteristics is provided at the treatment area. Also, since the sample holder 10 is positioned in contact with the outer surface 13 of the container 11, acoustic energy may be transmitted directly from the container 11 into the sample holder 10 and sample material, e.g., without transmitting acoustic energy through an air gap between the sample holder 10 and the container 11. (Note that in some embodiments, however, at least some air may be positioned in some locations between the container 11 and portions of the sample holder 10. That is, portions of the container 11 may be in contact with the sample holder 10, providing a transmission path for acoustic energy to the treatment area, while other portions of the container 11 may be out of contact with the sample holder 10, forcing acoustic energy to transmit though an air gap between the container 11 and the holder 10 to the treatment area.) The bottom shape of the holder 10 may have a lensing effect, or not, on the transmission of the acoustic energy to assist in the formation of the focal zone 17 or other effect.

While the coupling medium container 11 and its outer surface 13 (which is arranged to contact a sample holder) may be arranged is different ways, in this illustrative embodiment and as can be seen in FIG. 2, the coupling medium container 11 may include a cylindrical tube 16 with an outer surface 13 that contacts the sample holder 10 near the treatment area. In this embodiment, the cylindrical tube 16 is made of quartz or other suitable material, and has an outer diameter of about 4 inches and an inner diameter of about 3 inches, e.g., a wall thickness of about 0.5 inches. In other embodiments, the inner and outer diameters of the tube 16 may be different, e.g., where the tube is made of different materials. The cylindrical tube 16 may be hollow and completely filled with the coupling medium 4, such as an oil, distilled water or other liquid, or a semi-solid (e.g., gel) or solid (e.g., silica) material or mixture or other combination of materials. The outer surface 13 may include a resilient, acoustically transmissive material (such as a silicone rubber) having a thickness of about 0.120 inches. The resilient material at the outer surface 13 may conform to the lower surface of the sample holder 10 and thus help eliminate any air gaps or discontinuities that may affect transmission of acoustic energy to the treatment area. The resilient material may also help provide traction between the sample holder 10 and the container 11, e.g., to help resist slipping or other movement of the sample holder 10 relative to the outer surface 13 of the container 11. In addition, or alternately the material at the outer surface 13 may be thermally conductive, e.g., to help remove heat from the sample holder as necessary.

In accordance with an aspect of the invention, the outer surface of the coupling medium container may be rotatable with movement of the sample holder relative to the treatment area. For example, as the sample holder 10 is moved to the left (or right) relative to the focal zone 17 at the treatment area, the coupling medium container 11 may rotate about an axis 14. In this embodiment, the axis 14 may be a central longitudinal axis of the cylindrical tube 16 of the container 11, although other suitable axes are possible. Also, while the axis 14 in this embodiment may remain stationary as the container 11 rotates, the axis 14 may move up/down, left/right or in other directions with rotation of the container 11. Since the acoustic energy source 2 may move up/down or left/right with the container 11, movement of the axis 14 and container 11 may have no effect on the location of the focal zone 17 relative to the outer surface 13 of the container 11. For example, the container 11 may be mounted on hub-like end caps 15 that provide physical support for the container 11 while allowing the container 11 to rotate about the axis 14. The end caps 15 may be fixed to the cylindrical tube 16 and be supported on pins that allow the end caps 15 and cylindrical tube 16 to rotate. In such an embodiment, the acoustic energy source 2 may be supported on a gimbal or other suitable support that allows the source 2 to remain rotationally stationary while the container 11 rotates. However, the energy source 2 may move up/down or left/right with such movement of the container 11. Alternately, the end caps 15 may remain stationary, and the cylindrical tube 16 may rotate relative to the end caps 15. In this embodiment, the acoustic energy source 2 may be attached to one or both of the end caps and remain stationary relative to the container 11 as it rotates. A seal between the container 11 and the end caps may prevent leakage of the coupling medium 4 from the internal space 12 of the container 11, if necessary.

As noted above, the container 11 may take alternate forms than a cylindrical tube. For example, the coupling medium container 11 may be arranged to have an oval, rather than circular, cross section (as viewed in FIG. 2), and may have a kind of conveyor belt configured as the outer surface 13. Thus, an inner portion of the container 11 that holds the coupling medium 4 may remain stationary while the conveyor belt-type outer surface 13 rotates or otherwise moves around the inner container portion. Accordingly, not all portions of the container 11 need rotate or otherwise move with movement of the sample holder 10 at the treatment area. Instead, only an outer surface of the container that serves to help transmit acoustic energy from the source 2 to the sample holder 10 may move.

In one aspect of the invention, the outer surface of the coupling medium container may be rotatable or otherwise movable with linear movement of the sample holder relative to the treatment area. For example, as can be seen in FIG. 2, the sample holder 10 may move linearly along a table 3 and the container 11 may rotate about the axis 14. In this embodiment, the sample holder 10 may move in a direction parallel to a tangent of the outer surface 13, although the sample holder 10 may move along other paths, including a curved path. The outer surface 13 may rotate in response to movement of the sample holder 10, e.g., where a user or drive mechanism 5 moves the sample holder 10 along the table 3 and through the treatment area. That is, the outer surface 13 may engage the sample holder 10 so that as the sample holder 10 moves, the outer surface 13 rotates. Alternately, the outer surface 13 may be driven to rotate by a drive mechanism 5. This rotation of the outer surface 13 may cause the sample holder 10 to move relative to the treatment area, e.g., allowing user to place the sample holder 10 onto the table 3 and the sample holder to be automatically fed into the treatment area by the outer surface 13. The drive mechanism 5 may take any suitable form, such as a motor and associated gearing, drive chain and sprockets, a friction drive wheel attached to the motor that contacts the outer surface 13, a ball and screw device, and others. The drive mechanism 5 may include one or more sensors, such as a speed sensor that detects motion of the outer surface 13 and/or the sample holder 10. Feedback regarding speed, position or other characteristic regarding motion of the outer surface 13 and/or the sample holder 10 may be used by the controller 20 to control movement of the container 11 and/or the sample holder 10. For example, the controller 20 may control the drive mechanism 5 to rotate the outer surface 13 so that the sample holder 10 moves relative to the treatment area at a desired speed and/or to a desired position. Note that while in this embodiment, the outer surface 13 moves with the cylindrical tube of the container 11, the outer surface 13 may move independently of the cylindrical tube. That is, the outer surface 13 may be mounted on the cylindrical tube or other support of the container 11 for rotation about the axis 14 while other portions of the container 11 remain stationary. For example, in some embodiments, the outer surface 13 may be arranged as a kind of conveyor belt that moves relative to other portions of the container 11. The conveyor belt may follow a circular, oval, or other suitable path in its rotation.

In some embodiments, a roller 6 may be positioned to contact the sample holder 10, e.g., to help keep the sample holder 10 in contact with the coupling medium container 11. In FIGS. 1 and 2, the roller 6 is positioned above the treatment area and can press downwardly on the sample holder 10. This contact may help maintain the sample holder 10 in a desired position relative to the treatment area even as the sample holder 10 moves. In this embodiment, the roller 6 is arranged to rotate about an axis 61, although other configurations, such as a conveyor belt arrangement, a spring loaded skid plate, multiple wheels or other arrangements are possible. The roller 6 may be driven to rotate by the drive mechanism 5, or may be arranged as an idler roller that moves with movement of the sample holder 10. The roller 6 may be mounted to move relative to the outer surface 13, e.g., up and down as shown in FIG. 2, to accommodate sample holders 10 of different heights. For example, the roller 6 may have spring-loaded or compressed air-biased mount that biases the roller 6 toward the outer surface 13. Accordingly, the roller 6 may be capable of applying a relatively constant biasing force on the sample holder 10 even for sample holders of different heights. In some arrangements, the roller 6 may have a resilient material that contacts the sample holder 10, e.g., to help bias the holder 10 toward the outer surface 13 and/or provide a frictional engagement between the roller 6 and the holder 10. The roller 6 may have any suitable diameter, and may be larger or smaller than the coupling medium container 11.

In another aspect of the invention, heat may be exchanged between the coupling medium 4 and a heat exchanger 7. For example, the acoustic energy source 2 may generate heat that is ideally removed from the coupling medium 4, and a heat exchanger may be used to help keep the coupling medium 4, the container 11 and/or the sample holder 10 at a desired temperature. Where the coupling medium 4 is liquid, the coupling medium 4 may be circulated through a heat exchanger 7 to remove heat from (or provide heat to) the coupling medium 4. In other embodiments, the heat exchanger 7 may be located in the container 11, e.g., a single or multi-phase fluid may be circulated through an evaporator (or condenser) or other heat exchanger that is immersed in or otherwise thermally coupled to the coupling medium 4. In another arrangement, a heat exchanger in the form of a heat sink coupled to a thermoelectric device (such as a Peltier device) may be used to remove and/or provide heat with respect to the coupling medium 4 whether the coupling medium is liquid or solid. In yet another arrangement, a heat exchanger may include a heat pipe used to remove heat from the coupling medium 4, or to provide heat to the coupling medium 4. An evaporator (or condenser) portion of the heat pipe may be positioned in the container 11, while a condenser (or evaporator) portion of the heat pipe is positioned outside of the container 11. In some embodiments, controlling the temperature of the coupling medium 4 may help control the characteristics of the acoustic energy at the treatment area, e.g., by keeping the acoustic energy source 2 at a desired temperature range, by keeping the acoustic impedance of the coupling medium 4 in a desired range, and by minimizing the potential cavitation in the coupling medium 4, etc.

In some embodiments, the roller may include an inspection window to allow for visible inspection and/or other monitoring of sample material in the sample holder. For example, the roller 6 may be transparent to visible light or other electromagnetic radiation to allow for inspection and/or imaging of sample material in the sample holder 10. Inspection may be done by a human, e.g., by viewing an image captured by a suitably arranged sensor 62 such as a video camera, photodetector, IR detector, and so on, inside the roller 6 that images sample material in the holder 10. Alternately, the controller 20 may assess characteristics of the sample material, e.g., via image analysis or other assessment. Characteristics of the material in the sample holder 10 detected by the sensor 62 may be used by the controller 20 to control the acoustic energy source 2 or other components of the system 1. For example, if excessive cavitation is to be avoided, the controller 20 may adjust the acoustic energy at the focal zone if the sensor 62 detects the presence of cavitation bubbles of a certain size and/or number. Other features may be detected by the sensor 62, such as the size, density or other characteristics of particles in the sample holder 10 in the case where the acoustic treatment is intended to break down the size of particles in the sample material. Thus, the sensor 62 may detect whether acoustic treatment is progressing as desired and whether processing is complete, e.g., to trigger the introduction of additional sample material into the sample holder 10. The sensor 62 need not be positioned in the roller 6, and instead may be positioned in another location suitable to detect characteristics of sample material.

Figure 3:
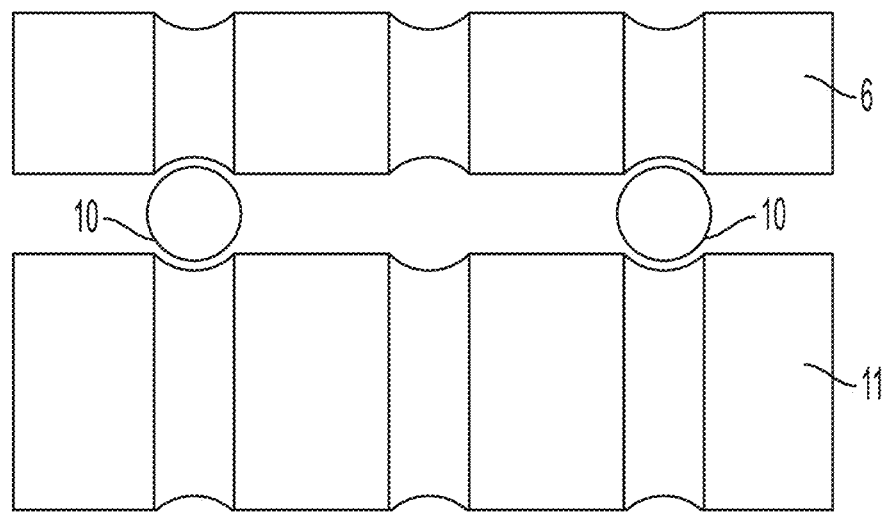
FIG. 3 is a front view of a coupling medium container and roller arranged to receive tube-shaped sample holders.

In some arrangements, the coupling medium container 11 and/or the roller 6 (if present) may be arranged to engage different types of sample holders 10 and/or to help maintain a sample holder stationary relative to the outer surface 13. For example, FIG. 3 shows an embodiment in which the outer surface 13 of the container 11 and the roller 6 are arranged with one or more circumferential grooves. This arrangement may help the system 1 receive and engage tube-shaped sample holders 10. For example, the tube shaped sample holders 10 may be laid on their side and fed into the space defined by the grooves of the roller 6 and the outer surface 13. In this way, the tube-shaped sample holders 10 can be reliably moved through the treatment zone (e.g., by driven rotation of the roller 6 and/or outer surface 13), and moreover, multiple tubes may be processed at the same time by a single system 1. Alternately, the system may be arranged to treat only a single tubular sample holder 10.

Figure 4:
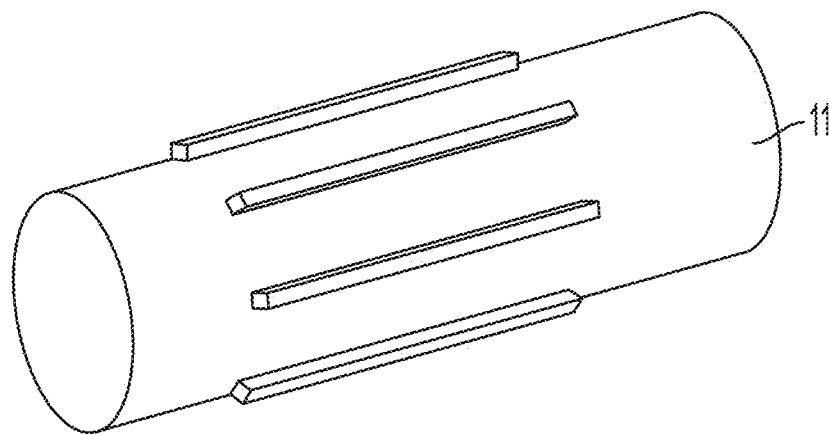
FIG. 4 shows a perspective view of a coupling medium container including an outer surface arranged to assist with maintaining a sample holder stationary relative to the outer surface.

In some embodiments, the container 11 and/or the roller 6 may be provided with interchangeable outer surface coverings, e.g., to allow the container 11 and/or roller 6 to be changed in configuration for interacting with different types of sample holders. For example, the outer surface 13 of the container 11 in FIG. 3 may be removed and exchanged for another outer surface 13, such as one with a smooth, flat surface arrange to engage a sample holder 10 having a smooth, flat surface. Other arrangements are possible, of course, and may depend on the arrangement of the sample holder 10. For example, FIG. 4 shows a container 11 with an outer surface 13 with axial ribs that extend along the outer surface 13. Such a configuration for the outer surface 13 may help keep the sample holder 10 from slipping or otherwise moving relative to the outer surface 13 during treatment. This may help ensure that different sample portions experience a suitable exposure to acoustic energy, e.g., spend a consistent amount of time at the treatment area.

Transducer

In certain embodiments, the sonic energy source 2 may include, for example, an ultrasound transducer or other transducer, that produces acoustic waves in the "ultrasonic" frequency range. Ultrasonic waves start at frequencies above those that are audible, typically about 20,000 Hz or 20 kHz, and continue into the region of megahertz (MHz) waves. The speed of sound in water is about 1500 meters per second, and hence the wavelength of a 1500 Hz wave in water is about a meter, typically too long for specific focusing on individual areas less than one centimeter in diameter, although usable in non-focused field situations. At 20 kHz the wavelength is about 7.5 cm in water, which is effective in relatively small treatment vessels. Depending on the sample and vessel volume, preferred frequencies may be higher, for example, about 100 kHz, about 1 MHz, or about 10 MHz, with wavelengths, respectively, of approximately 1.0, 0.1, and 0.01 cm. In contrast, for conventional sonication, including to sonic welding, frequencies are typically approximately in the tens of kHz, and for imaging, frequencies are more typically about 1 MHz and up to about 100 MHz. In lithotripsy, repetition rates of pulses are fairly slow, being measured in the hertz range, but the sharpness of the pulses generated give an effective pulse wavelength, or in this case, pulse rise time, with frequency content up to about 100 to about 300 MHz, or 0.1-0.3 gigahertz (GHz).

The frequency used in certain embodiments of the invention also will be influenced by the energy absorption characteristics of the sample or of the sample holder 10, for a particular frequency. To the extent that a particular frequency is better absorbed or preferentially absorbed by the sample material, it may be preferred. The energy can be delivered in the form of short pulses or as a continuous field for a defined length of time. The pulses can be bundled or regularly spaced.

A generally vertically oriented focused ultrasound beam may be generated in several ways by the acoustic energy source 2. For example, a single-element piezoelectric transducer, such as those supplied by Sonic Concepts, Woodinville, Wash., that can be a 1.1 MHz focused single-element transducer, can have a spherical or other curved transmitting surface that is oriented such that the focal axis is vertical.

Another embodiment uses a flat unfocused transducer and an acoustic lens or waveguide to focus the beam. Still another embodiment uses a multi-element transducer such as an annular array in conjunction with focusing electronics to create the focused beam. The annular array potentially can reduce acoustic sidelobes near the focal point by means of electronic apodizing, that is by reducing the acoustic energy intensity, either electronically or mechanically, at the periphery of the transducer. This result can be achieved mechanically by partially blocking the sound around the edges of a transducer or by reducing the power to the outside elements of a multi-element transducer. This reduces sidelobes near the energy focus, and can be useful to reduce heating of the sample holder 10. Alternatively, an array of small transducers can be synchronized to create a converging beam. Still another embodiment combines an unfocused transducer with a focusing acoustic mirror to create the focused beam. This embodiment can be advantageous at lower frequencies when the wavelengths are large relative to the size of the transducer. The axis of the transducer of this embodiment can be horizontal and a shaped acoustic mirror used to reflect the acoustic energy vertically and focus the energy into a converging beam.

In certain embodiments, the focal zone can be small relative to the dimensions of the sample holder 10 to avoid heating of the sample holder 10. In one embodiment, the focal zone has a width of approximately 1 mm. Heating of the sample holder 10 can be reduced by minimizing acoustic sidelobes near the focal zone. Sidelobes are regions of high acoustic intensity around the focal point formed by constructive interference of consecutive wavefronts. The sidelobes can be reduced by apodizing the transducer either electronically, by operating the outer elements of a multi-element transducer at a lower power or exciting periphery region of single element with lower electrical power, or mechanically, by partially blocking the acoustic waves around the periphery of a single element transducer. Sidelobes may also be reduced by using short bursts, for example in the range of about 3 to about 5 cycles in the treatment protocol.

The transducer can be formed of a piezoelectric material, such as a piezoelectric ceramic. The ceramic may be fabricated as a "dome", which tends to focus the energy. One application of such materials is in sound reproduction; however, as used herein, the frequency is generally much higher and the piezoelectric material would be typically overdriven, that is driven by a voltage beyond the linear region of mechanical response to voltage change, to sharpen the pulses. Typically, these domes have a longer focal length than that found in lithotriptic systems, for example, about 20 cm versus about 10 cm focal length. Ceramic domes can be damped to prevent ringing or undamped to increase power output. The response is linear if not overdriven. The high-energy focus zone of one of these domes is typically cigar-shaped. At 1 MHz, the focal zone is about 6 cm long and about 2 cm wide for a 20 cm dome, or about 15 mm long and about 3 mm wide for a 10 cm dome. The peak positive pressure obtained from such systems is about 1 MPa (mega Pascal) to about 10 MPa pressure, or about 150 PSI (pounds per square inch) to about 1500 PSI, depending on the driving voltage. The focal zone, defined as having an acoustic intensity within about 6 dB of the peak acoustic intensity, is formed around the geometric focal point. It is also possible to generate a line-shaped focal zone, e.g., that spans the width of a multi-well plate and enables the system 1 to treat multiple wells simultaneously.

The wavelength, or characteristic rise time multiplied by sound velocity for a shock wave, is in the same general size range as a biological cell, for example about 10 to about 40 micron. This effective wavelength can be varied by selection of the pulse time and amplitude, by the degree of focusing maintained through the interfaces between the source and the material to be treated, and the like.

Another source of focused acoustic pressure waves is an electromagnetic transducer and a parabolic concentrator, as is used in lithotripsy. The excitation of such devices tends to be more energetic, with similar or larger focal regions. Strong focal peak negative pressures of about −16 MPa have been observed. Peak negative pressures of this magnitude provide a source of cavitation bubbles in water, which can be desirable in an extraction process.

Drive Electronics and Waveform Control.

One treatment protocol for treating material with acoustic energy in the sample holder 10 can include variable acoustic waveforms combined with sample motion and positioning to achieve a desired effect. The acoustic waveform of the transducer may have many effects, including: acoustic microstreaming in and near cells due to cavitation, that is flow induced by, for example, collapse of cavitation bubbles; shock waves due to nonlinear characteristics of the wave propagation and fluid bath; shock waves due to cavitation bubbles; thermal effects, which lead to heating of the sample, heating of the sample vessel, and/or convective heat transfer due to acoustic streaming; flow effects, causing deflection of sample material from the focal zone due to shear and acoustic pressure, as well as mixing due to acoustic streaming, that is flow induced by acoustic pressure; and chemical effects. The waveform of focused sound waves can be a single shock wave pulse, a series of individual shock wave pulses, a series of shock wave bursts of several cycles each, or a continuous waveform. Incident waveforms can be focused directly by either a single element, such as a focused ceramic piezoelectric ultrasonic transducer, or by an array of elements with their paths converging to a focus. Alternatively, multiple foci can be produced to provide ultrasonic treatment to multiple treatment zones, vessels, or wells. Additionally, the flow of the sample material into, or out of the processing sample holder 10 can interact with the acoustic effects, and the acoustic streaming can be modified to enhance this sample flow in a desirable manner.

The treatment protocol can be optimized to maximize energy transfer while minimizing thermal and flow effects. The treatment protocol also can effectively mix the contents of the sample holder 10, in the case of a particulate sample suspended in a liquid. Energy transfer into the sample can be controlled by adjusting the parameters of the acoustic wave such as frequency, amplitude, and cycles per burst. Temperature rise in the sample can be controlled by limiting the duty cycle of the treatment and by optimizing heat transfer between the sample holder 10 and the container 11/coupling medium 4. Heat transfer can be enhanced by making the sample holder 10 with thin walls, of a relatively highly thermally conductive material (e.g., to transfer heat to a highly thermally conductive outer surface 13 of the container 11), and/or by promoting forced convection by acoustic streaming in the sample holder 10.

For example, for a cellular disruption and extraction treatment, an example of an effective energy waveform is a high amplitude sine wave of about 1000 cycles followed by a dead time of about 9000 cycles, which is about a 10% duty cycle, at a frequency of about 1.1 MHz. The sine wave electrical input to the transducer typically results in a sine wave acoustic output from the transducer. As the focused sine waves converge at the focal point, they can become a series of shock waves due to the nonlinear acoustic properties of the water or other fluid in the coupling medium 4. This protocol treats the material in the focal zone effectively during the "on" time. As the material is treated, it is expelled from the focal zone and new material circulates into the focal zone. The acoustic "on" and "off" times can be cycled to be effective, for example, for extracting the cellular contents of ground or particulate leaf tissue, while causing minimal temperature rise in the treatment vessel.

Further advantage in disruption and other processes may be gained by creating a high power "treat" interval alternating with a low power "mix" interval. More particularly, in this example, the "treat" interval utilizes a sine wave that has a treatment frequency, a treatment cycles-per-burst count, and a treatment peak-to-peak amplitude. The "mix" interval has a mix frequency, a mix cycles-per-burst count and a lower mix peak-to-peak amplitude. Following each of the intervals is a dead time. Of course, these relationships are merely one example of many, where one interval in considered to be high power and one interval is considered to be low power, and these variables and others can be altered to produce more or less energetic situations. Additionally, the treat function or interval and the mix function or interval could emit from different or multiple transducers in the same apparatus, optionally emitting at different frequencies.

High power/low power interval treatments can allow multiple operations to be performed, such as altering permeability of components, such as cells, within the sample followed by subsequent mixing of the sample. The treat interval can maximize cavitation and bioeffects, while the mix interval can maximize mixing within the treatment vessel and/or generate minimal heat. Adding a longer, high power "super-mix" interval occasionally to stir up particles that are trapped around the periphery of the sample holder 10 can provide further benefits. This "super-mix" interval generates additional heat, so it is programmed to treat infrequently during the process, for example, every few seconds. Additionally, dead times between the mix and treat intervals, during which time substantially no energy is emitted from the sonic energy source, can allow fresh material to circulate into the energy focal zone of the target.

The waveform of the sound wave typically is selected for the particular material being treated. For example, to enhance cavitation, it can be desirable to increase the peak negative pressure following the peak positive pressure. For other applications, it can be desirable to reduce cavitation, but maintain the peak positive pressure. This result can be achieved by performing the process in a pressurized sample holder 10 at a slight pressure above ambient. For example, if the waveform generated has a peak negative pressure of about −5 MPa, then the entire chamber may be pressurized to about 10 MPa to eliminate cavitation from occurring during the process. Material to be treated can be pressurized on a batch or a continuous basis within the sample holder 10.

Typically, the shock wave is characterized by a rapid shock front with a positive peak pressure in the range of about 15 MPa, and a negative peak pressure in the range of about negative 5 MPa. This waveform is of about a few microseconds duration, such as about 5 microseconds. If the negative peak is greater than about 1 MPa, cavitation bubbles may form. Cavitation bubble formation also is dependent upon the surrounding medium. For example, glycerol is a cavitation inhibitive medium, whereas liquid water is a cavitation promotive medium. The collapse of cavitation bubbles forms "microjets" and turbulence that impinge on the surrounding material.

Control of the acoustic energy source 2 may be performed by the controller 20 using a feedback control mechanism so that any of accuracy, reproducibility, speed of processing, control of temperature, provision of uniformity of exposure to sonic pulses, sensing of degree of completion of processing, monitoring of cavitation, and control of beam properties (including intensity, frequency, degree of focusing, wave train pattern, and position), can enhance performance of the treatment system 1. A variety of sensors or sensed properties may be used by the controller 20 for providing input for feedback control. These properties can include sensing of temperature of the sample material; sonic beam intensity; pressure; coupling medium properties including temperature, salinity, and polarity; sample material position; conductivity, impedance, inductance, and/or the magnetic equivalents of these properties, and optical or visual properties of the sample material. These optical properties, which may be detected by the sensor 62 typically in the visible, IR, and UV ranges, may include apparent color, emission, absorption, fluorescence, phosphorescence, scattering, particle size, laser/Doppler fluid and particle velocities, and effective viscosity. Sample integrity or comminution can be sensed with a pattern analysis of an optical signal from the sensor 62. Particle size, solubility level, physical uniformity and the form of particles could all be measured using instrumentation either fully stand alone sampling of the fluid and providing a feedback signal, or integrated directly with the focused acoustical system via measurement interface points such as an optical window. Any sensed property or combination thereof can serve as input into a control system. The feedback can be used to control any output of the system, for example beam properties, sample position or flow in the sample holder 10, treatment duration, and losses of energy at boundaries and in transit via reflection, dispersion, diffraction, absorption, dephasing and detuning.

According to certain embodiments of the present invention, several aspects of the treatment system 1 can enhance the reproducibility and/or effectiveness of particular treatments using ultrasonic energy in in vitro applications, where reproducibility, uniformity, and precise control are desired. These aspects include the use of feedback, precise focusing of the ultrasonic energy, monitoring and regulating of the acoustic waveform (including frequency, amplitude, duty cycle, and cycles per burst), positioning of the sample holder 10 relative to the ultrasonic energy so that the sample material is uniformly treated, controlling movement or flow of the sample relative to the focus of ultrasonic energy during a processing step, and/or controlling the temperature of the sample being treated, either by the ultrasonic energy parameters or through the use of temperature control devices such as a water bath. A treatment protocol can be optimized, using one or a combination of the above variables, to maximize, for example, shearing, extraction, permeabilization, comminution, stirring, or other process steps, while minimizing undesirable thermal effects.

In one embodiment of the invention, high intensity ultrasonic energy is focused on a sample holder 10, and "real time" feedback relating to one or more process variables is used to control the process. In another embodiment, the process is automated and is used in a high throughput system, such as a continuous flowing stream of material to be treated, optionally segmented.

In certain embodiments, the processing system can include a high intensity transducer that produces acoustic energy when driven by an electrical or optical energy input;

a device or system for controlling excitation of the transducer, such as an arbitrary waveform generator, an RF amplifier, and a matching network for controlling parameters such as time, intensity, and duty cycle of the ultrasonic energy; a system or method for transferring material into and out of the process zone, either actively or passively, to allow automation and the implementation of feedback from monitoring; a temperature sensor; a device for controlling temperature; one or more reaction chambers 10; and a sensor for detecting, for example, optical, radiative, and/or acoustic signatures. The feedback signal can also come from a signal provided by either external or integrated measurement methods such as particle size, solubility, and form factors.

Temperature, Cavitation, Particle Size, Solubility, and Pressure Management and Control A. Visual Monitoring of the Sample Optical or video detection and analysis can be employed to optimize treatment of the sample. For example, in a suspension of biological tissue, the viscosity of the mixture can increase during treatment due to the diminution of the particles by the treatment and/or by the liberation of macromolecules into the solution. Video analysis of the sample during treatment allows an automated assessment of the mixing caused by the treatment protocol. The protocol may be modified during the treatment to promote greater mixing as a result of this assessment. The video data may be acquired and analyzed by the computer control system (i.e., part of the controller 20) that is controlling the treatment process. Other optical measurements such as spectral excitation, absorption, fluorescence, emission, and spectral analysis also can be used to monitor treatment of the sample, whether in the sample holder 10 at the treatment area or elsewhere. A laser beam, for example, can be used for alignment and to indicate current sample position.

B. Temperature Control

Certain applications require that the temperature of the sample being processed be managed and controlled during processing. For example, many biological samples should not be heated above 4 degrees C. during treatment. Other applications require that the samples be maintained at a certain elevated temperature during treatment. The ultrasound treatment protocol influences the sample temperature in several ways: the sample absorbs acoustic energy and converts it to heat; the sample treatment chamber absorbs acoustic energy and converts it to heat which, in turn, can heat the sample; and acoustic streaming develops within the sample treatment chamber, forcing conductive heat transfer between the sample treatment chamber and the container/coupling medium through the interface between the two.

The acoustic waves or pulses can be used to regulate the temperature of the solutions in the treatment chamber. At low power, the acoustic energy produces a slow stirring without marked heating. Although energy is absorbed to induce the stirring, heat may be lost rapidly through the sides of the treatment chamber, resulting in a negligible equilibrium temperature increase in the sample. At higher energies, more energy is absorbed, and the temperature rises. The degree of rise per unit energy input can be influenced and/or controlled by several characteristics, including the degree of heat absorption by the sample or the treatment chamber and the rate of heat transfer from the treatment chamber to its surroundings (e.g., the coupling medium). Additionally, the treatment protocol may alternate a high-powered treatment interval, in which the desired effects are obtained, with a low power mixing interval, in which acoustic streaming and convection are achieved without significant heat generation. This convection may be used to promote efficient heat exchange or cooling.

The sample temperature may be required to remain within a given temperature range during a treatment procedure. Temperature can be monitored remotely by, for example, an infra-red sensor. Temperature probes such as thermocouples may not be particularly well suited for all applications because the sound beam may interact with the thermocouple and generate an artificially high temperature in the vicinity of the probe. Temperature can be monitored by the same controller 20 that controls the acoustic waveform. The control responds to an error signal which is the difference between the measured actual temperature of the sample and the target temperature of the sample. The control algorithm can be as a hysteritic bang-bang controller, such as those in kitchen stoves, where, as an output of the control system, the acoustic energy is turned off when the actual temperature exceeds a first target temperature and turned on when the actual temperature falls below a second target temperature that is lower than the first target temperature. More complicated controllers can be implemented. For example, rather than simply turning the acoustic signal on and off, the acoustic signal could continuously be modulated by a more advanced PID control algorithm, for example, by varying the amplitude or the duty cycle, to provide finer temperature regulation.

In the application of a bang-bang control algorithm for a multiple sample format, once a maximum temperature value has been exceeded and the sonic energy is turned off for a particular sample, an alternative to waiting for the sample to cool below a selected temperature before turning the sonic energy on again, is to move on to the next sample, or increase the flow rate of new sample material into the treatment chamber. Another alternative is to switch to a predefined "cooling" waveform which promotes convection without adding significant heat to a particular sample, and synchronizing this cycle with the introduction of new sample material to the chamber.

C. Cavitation Control

In some applications, it can be preferable to treat the sample with as much energy as possible without causing cavitation. This result can be achieved by suppressing cavitation. Cavitation can be suppressed by pressurizing the treatment chamber above ambient, often known as "overpressure," to the point at which no negative pressure develops or negative pressure is higher than the cavitation threshold of the medium during the rarefaction phase of the acoustic wave. This suppression of cavitation is beneficial in applications such as cell transformation where the desired effect is to open cellular membranes while maintaining viable cells. In other applications it may be desirable to enhance cavitation. In these applications, a "negative" overpressure or vacuum can be applied to the region of the focal zone.

The control of cavitation in the sample also can be important during acoustic treatment processes. In some scenarios, the presence of small amounts of cavitation may be desirable to enhance biochemical processes; however, when large numbers of cavitation bubbles exist they can scatter sound before it reaches the target, effectively shielding the sample.

Cavitation can be detected by a variety of methods, including acoustic and optical methods. An example of acoustic detection is a passive cavitation detector (PCD) which includes an external transducer that detects acoustic emissions from cavitation bubbles. (That is, the PCD may be external to the sample holder 10, e.g., the PCD may be located in the coupling medium 4.) The signal from the PCD can be filtered, for example using a peak detector followed by a low pass filter, and then input to a controlling computer (part of controller 20) as a measure of cavitation activity. The acoustic signal could be adjusted in ways similar to those described in the temperature control example to maintain cavitation activity at a desired level.

Overpressure: Increased pressure in the sample holder 10 is one technique for controlling cavitation. Overpressure tends to remove cavitation nuclei and increases the energy level required to create cavitation. Motes in the fluid are strongly affected by overpressure and so cavitation in free-fluid is often dramatically reduced, even by the addition of one atmosphere of overpressure. Nucleation sites on the sample holder 10 walls tend to be more resistant to overpressure; however the cavitation tends to be restricted to these sites and any gas bubbles that float free into the free-fluid are quickly dissolved. By increasing the ambient pressure of the system, the pressures required for bubble nucleation and collapse increase, thus increasing the force imparted by collapse of the cavitation bubble. This relationship is roughly linear—that is, doubling the ambient pressure of the system doubles the resulting force of bubble collapse. Careful system design to accommodate higher overall pressures can allow this to scale by many factors. Overpressure may be applied to the sample holder 10 by the roller 6 and the container 11, e.g., by squeezing the sample holder 10 and thereby increasing a pressure of a chamber in which sample material is held. In one embodiment, the sample holder 10 may include a plunger at each sample volume that can be pressed by the roller 6 to increase the pressure in the sample volume.

Degassing: Reducing the gas content of the material fluid tends to reduce cavitation, again by reducing cavitation nuclei and making it harder to initiate cavitation. Another method of controlling cavitation or the effects of cavitation is to control the gasses that are dissolved in the sample fluid. For instance, cavitation causes less mechanical damage in fluid saturated with helium gas than in fluid saturated with argon gas.

D. Monitoring of Cavitation

A variety of methods may be employed to detect cavitation. For example, acoustic emissions, optical scattering, high-speed photography, mechanical damage, and sonochemicals can be used. As described above for monitoring temperature, information from cavitation detection can be used by the system to produce an output that selectively controls exposure of a sample to sonic energy in response to the information. Each of these methods to monitor cavitation are described more fully below.

Acoustic emissions: Bubbles are effective scatterers of ultrasound. The pulsation mode of a bubble is referred to as monopole source, which is an effective acoustic source. For small, generally linear oscillations, the bubble simply scatters the incident acoustic pulse. However, as the response becomes more nonlinear, it also starts to emit signals at higher harmonics. When driven harder, the bubbles start to generate subharmonics as well. Eventually as the response becomes a periodic or chaotic, the scattered field tends towards white noise. In the scenario where inertial collapses occur, short acoustic pressure pulses are emitted. An acoustic transducer can be configured to detect these emissions. There is a detectable correlation between the onset of the emissions and cell disruption.

Optical scattering: Bubbles also scatter light. When bubbles are present, light is scattered. Light can normally be introduced into the system using fiber optic light sources so that cavitation can be detected in real-time, and therefore can be controlled by electronic and computer systems.

High-speed photography: Bubbles can be photographed. This method typically requires high-speed cameras and high intensity lighting, because the bubbles respond on the time frame of the acoustics. It also requires good optical access to the sample under study. This method can give detailed and accurate data and may be a consideration when designing systems according to the invention. Stroboscopic systems, which take images far less frequently, can often give similar qualitative performance more cheaply and easily than high-speed photography.

Mechanical damage: Cavitation is known to create damage to mechanical systems. Pitting of metal foils is a particularly common effect, and detection method. There is a correlation between the cavitation needed to pit foils and to disrupt cells.

Sonochemicals: A number of chemicals are known to be produced in response to cavitation. The yield of these chemicals can be used as a measure of cavitational activity. A common technique is to monitor light generation from chemicals, such as luminol, that generate light when exposed to cavitation. Sonochemical yield usually can not be done during cell experiments but can be done independently under identical conditions, and thereby, provide a calibrated standard.

Materials for Treatment

A. Biological Materials

Many biological materials can be treated according the present invention. For example, such materials for treatment include, without limitation, growing plant tissue such as root tips, meristem, and callus, bone, yeast and other microorganisms with tough cell walls, bacterial cells and/or cultures on agar plates or in growth media, stem or blood cells, hybridomas and other cells from immortalized cell lines, and embryos. Additionally, other biological materials, such as serum and protein preparations, can be treated with the processes of the invention, including sterilization.

B. Binding Materials

Many binding reactions can be enhanced with treatments according to the invention. Binding reactions involve binding together two or more molecules, for example, two nucleic acid molecules, by hybridization or other non-covalent binding. Binding reactions are found, for example, in an assay to detect binding, such as a specific staining reaction, in a reaction such as the polymerase chain reaction where one nucleotide molecule is a primer and the other is a substrate molecule to be replicated, or in a binding interaction involving an antibody and the molecule it binds, such as an immunoassay. Reactions also can involve binding of a substrate and a ligand. For example, a substrate such as an antibody or receptor can be immobilized on a support surface, for use in purification or separation techniques of epitopes, ligands, and other molecules.

C. Chemical and Mineral Materials

Organic and inorganic materials can be treated with controlled acoustic pulses according to the methods of the invention. The sonic pulses may be used to commute a solid material, particularly under a feedback control regime, or in arrays of multiple samples. As with biological samples, individual organic and inorganic samples in an array can be treated in substantial isolation from the laboratory environment. Beside altering their physical integrity, materials can be dissolved in solvent fluids, such as liquids and gasses, or extracted with solvents. For example, dissolution of polymers in solvents can be very slow without stirring, but stirring multiple samples with current methods is difficult and raises the possibility of cross-contamination between samples. However, stirring of multiple samples without cross-contamination between samples can be accomplished with apparatus and methods of the present invention.

Treatment Applications

A. Altering Cell Accessibility

According to the invention, controlled sonic pulses in a medium may be used to treat a sample containing biological material. The pulses can be specifically adapted to preferentially interact with supporting matrices in a biological material, such as plant cell walls or extracellular matrices such as bone or collagen, thereby lessening or removing a barrier function of such matrices and facilitating the insertion of extracellular components into a cell. In this application, the cell is minimally altered and cell viability is preserved. These pulses can be caused by shock waves or by sound waves. The waves can be created external to the sample, or directly in the sample, via applied mechanical devices. In experiments where thermal effects are negligible, there typically is no lysis, unless cavitation is present. Other modes of sonic energy can have different effects than disrupting a matrix and can be used either with pre-treatment, with disrupting sonic energy, or by themselves. For, example the conditions to disrupt a matrix can be different from those to permeabilize a cell membrane.

There are many possible mechanisms by which cavitation may affect cells and there is no consensus as to which mechanisms, if any, dominate. The principle mechanisms are thought to include shear, microjets, shock waves, sonochemistry, and other mechanisms.

B. Extracting

In a variation of the method to alter cellular accessibility described above, controlled pulses in a medium can be used to treat a sample containing biological material to extract a fraction or fractions of the biological material. The pulses are specifically adapted to preferentially interact with supporting matrices, such as plant cell walls or extracellular matrices such as bone or collagen, or materials having differences in rigidity or permeability in a biological material, thereby lessening or removing a barrier function of such matrices or materials. These pulses can be caused by shock waves or by sound waves. The waves can be created external to the sample, or directly in the sample, via applied mechanical means.

The supporting matrix of a biological sample can be disrupted without disrupting one or more selected internal structures of the cells contained within the matrix. Representative examples of such samples are: i) bone, in which a rigid matrix contains living cells of interest; ii) mammalian tissue samples, which contain living cells embedded in a matrix of elastic connective tissue and "glycocalyx" or intercellular matrix; and iii) plant tissues, such as leaves, which contain cells in a matrix of cellulose, often cross-linked with other materials, of moderate rigidity. Virtually all living cells are gelatinous in texture, and can be deformed to some extent without rupture or internal damage. Matrices, in contrast, are designed to support and protect cells, as well as to achieve other biological functions. In the three examples above, the matrices of bone and leaves are designed to provide rigidity to the structure, while the support of most collagenous matrices has a strongly elastic character. Thus, different protocols for example, amplitude, duration, number of pulses, and temperature of sample, may be used to disrupt different matrices by mechanical means without damaging the cellular material.

Three areas to optimize for extraction are treatment waveform, mixing waveform, and positioning or dithering. One method to determine the appropriate treatment and positioning parameters for a target sample for extraction purposes is described below.

First, a solid sample is placed in a volume of liquid in about a 1:1 ratio (weight/volume), in a treatment chamber. For example, 0.25 ml of methanol is added to 0.25 gm of leaf tissue in a 0.5 ml treatment chamber. A single sample is placed within the focal zone of the sonic apparatus. Without using the treatment protocol, the mixing waveform is adjusted to provide "stirring" of the sample at the lowest amplitude, fewest cycles/burst, and lowest duty cycle. After the mixing waveform protocol is defined, the disruption treatment waveform is adjusted by immobilizing the target sample in the focal zone such that there is no mixing and no sample movement, such as dithering. Using a sonic energy source such as a piezoelectric transducer, the sample is subjected to a minimum number of cycles per burst, for example, three. For extraction purposes, the amplitude is initially used with a nominal 500 mV setting. A portion of the sample is treated and inspected under a microscope for signs of membrane disruption. Such inspection can be done in conjunction with dyes that stain intracellular organelles. The number of cycles/burst is then increased until a particular desired tissue disruption level is achieved in the immobilized portion of tissue. With a fresh sample, and with a 1:1 ratio of tissue to liquid, the temperature of the sample is monitored during a million cycle total treatment with an infra-red sensor directed to the top of a thin polyethylene film covering the sample vessel. The duty cycle is adjusted to keep the temperature within predefined ranges, such as 4 degrees C. within +/−2 degrees C.

C. Introducing a Molecule into or Removing a Molecule from a Cell

Once a sample having a matrix has been sufficiently weakened or attenuated, but not to the point where a substantial number of cells contained within the matrix are killed or lysed, an exposed target cell or cells become amenable to insertion of exogenous molecules by techniques such as transfection or transformation. With some matrices, it may be convenient to isolate the cells from the matrices and then to transfect the cells. In other cases, it will be preferable, particularly in an automated system, to perform the transfection directly on the treated tissue sample, using solutions and conditions adapted from known techniques. Alternatively, in situations where a cell to be treated is not situated within a matrix, the cell can be directly treated according to the process below without having to pre-treat the matrix. While the treatment below is described mainly for transfection, methods and apparatus according to the present invention are equally applicable to a transformation process or other processes to introduce an exogenous material into a permeabilized cell membrane.

The waveforms used to alter the permeability of a cell are refined depending on the particular application. Typically, the shock wave is characterized by a rapid shock front with a positive peak pressure, for example about 100 MPa, and a negative peak pressure, for example about negative 10 MPa. This waveform is of a few microsecond duration, on the order of about 5 microseconds. If the negative peak is greater than about 1 MPa, cavitation bubbles may form. Cavitation bubble formation is also dependent upon the surrounding medium. For example, glycerol is a cavitation inhibitive medium; whereas, liquid water is a cavitation promotive medium. The collapse of cavitation bubbles forms "microjets" and turbulence that impinge on the surrounding material.

Sound waves, namely acoustic waves at intensities below the shock threshold, provide an alternative means of disrupting the matrix to allow access to the plasma membranes of the cells to allow transformation. Such sound waves can be generated by any known process. As biological material is subjected to subzero temperatures, for example about negative 5 degrees C., most but not all of the water is in the solid phase. However, in certain biological tissues microdomains of liquid water still remain for several reasons, such as natural "antifreeze" molecules or regions of higher salt concentration. Therefore, as a sample temperature is varied during the treatment with sound or shock waves, microdomains of liquid water are able to form shock waves and induce cavitation bubble formation and collapse, with the resultant shear stresses that impinge on surrounding tissues. Indeed, gradual alteration of the sample temperature can be desirable, as it provides focused domains of liquid water for impingement on the surrounding material. The waves can be applied to the samples either directly, as piezoelectric pulses, or via an intervening medium. This medium may be water, buffer, stabilizing medium for the target material to be isolated, or extraction medium for the target. An intervening medium also can be a solid, formed of a material which is intrinsically solid, or of a frozen solution.

At that point, or, optionally, previously, a solution or suspension containing the material to be incorporated into the cells is added to the sample. In one embodiment, the exogenous material is incorporated into the cells in a conventional manner, as is known in the art for cells with exposed plasma membranes. In another embodiment, acoustic energy is used to transiently permeabilize a plasma membrane to facilitate introduction of exogenous materials into the cells. The exogenous material may be present in the sample during the weakening of the matrix by acoustic energy. Even when the cells remain intact, as determined by dye exclusion or other viability measurements, the process of weakening the cell matrix by acoustic energy transiently destabilizes the plasma membranes, increasing the uptake of exogenous macromolecules and structures. If a further increase in the rate of incorporation is needed, then the intensity or time of application of acoustic energy is slightly increased until the cell membrane becomes transiently permeable. For example, a gentle pulse or wave is applied to the mixture, with a predetermined amplitude. This amplitude can be determined readily in separate experiments on samples of the same type to transiently make a plasma membrane of a cell type porous, in a similar empirical manner to the steps described above for determining an appropriate treatment to disrupt a matrix. During the transient porous state, exogenous materials diffuse into the cell and the materials are trapped there once the sonic or shock pulse is removed.

A major advantage of these methods for transfection, or other incorporation of exogenous material into living cells, is that the methods are readily amenable to scale-up, to automation, and to marked reduction in sample size and reagent volume. Thus, the methods are adaptable to large scale automation, in large part because they do not require the isolation of the cells from their matrix.

The number of cells per ml of media is also important factor for cellular applications to use acoustics effectively the concentration of the cells should not be too low (as the energy generated and utilized depends on the concentration of cells) or too high (viscosity is high). Additionally, with the process of permeabilization and with the mixing profile, other techniques of gene transfer may be augmented. Examples include, calcium phosphate coprecipitation, electroporation, and receptor-dependent processes.

D. Sterilizing

The terms "sterilize," "disinfect," "preserve," decontaminate," "inactivation," "disinfect," and "kill" are used interchangeably herein, unless otherwise demanded by the context. "Sterilization," namely killing of all organisms, may not be synonymous in certain operations with "decontamination," for example, when the contaminant is non-living, such as a protein or prion. These terms, typically, mean the substantial elimination of or interference with any activity of a particular organism and/or particle.

Methods for permeabilization and extraction, described above, can be modified to sterilize a sample. The apparatus and methods for sterilizing can be optimized for efficient sterilization of particular materials in particular volumes and containers. For a particular material to be sterilized, an initial set of conditions is selected. Such conditions can include selection of a type of sonic pulse generator, intensity of sonic energy, frequency of sonic energy, where relevant, and/or like variables. The conditions also can include volume, mode of transport, and/or exposure of the materials to be sterilized. Then, the initial conditions and near variants are applied to the sample, and the percentage of cells or viruses killed is determined by standard assay conditions. Further variables are selected for change. Accordingly, a zone of maximal killing of the test organism is found. Finally, other variables, such as flow rate and/or length and/or intensity of sonic exposure, are optimized to provide both a technical solution and a commercially useful solution to the problem of sterilizing a particular material. Any of these empirically determined values can be programmed into a control system of an apparatus used for sterilization to actively control sterilization, or the apparatus can have these values previously determined such that a user need only select a predetermined sterilization mode an the apparatus.

For many liquids, adequate sterilization is provided by destroying the cell walls of bacteria, fungi, and other living cells. This result is accomplished by using frequencies and wavelengths of sound which preferentially excite the membranes of the cells while minimally heating the solution until the cells are lysed. In most cellular organisms, opening the membrane and allowing the contents to mix with an extracellular fluid will kill the organism.

Viruses can be opened to the solution by similar processing. In the case of viruses, exposure of their internal nucleic acid to the solution may not be adequate to completely inactivate them, since the naked DNA or RNA can also be infectious. Adjuncts such as iodine or nucleic-acid digesting enzymes in the solution can be provided to complete the inactivation of the viruses.

E. Mixing, Stirring, and Heating

A fluid sample can be mixed controllably using the systems described herein. No direct contact between the material to be mixed and the sonic energy source is required. When the material to be mixed is in a treatment chamber, the treatment chamber itself is not necessarily touched by the source and is typically coupled to the source by a coupling medium.

F. Enhancing Reactions and Separations

In certain embodiments, temperature, mixing, or both can be controlled with ultrasonic energy to enhance a chemical reaction. For example, the association rate between a ligand present in a sample to be treated and an exogenously supplied binding partner can be accelerated. In another example, an assay is performed where temperature is maintained and mixing is increased to improve association of two or more molecules compared to ambient conditions. It is possible to combine the various aspects of the process described herein by first subjecting a mixture to heat and mixing in order to separate a ligand or analyte in the mixture from endogenous binding partners in the mixture. The temperature, mixing, or both, are changed from the initial condition to enhance ligand complex formation with an exogenously supplied binding partner relative to ligand/endogenous binding partner complex formation at ambient temperature and mixing. Generally, the second temperature and/or mixing conditions are intermediate between ambient conditions and the conditions used in the first separating step above. At the second temperature and mixing condition, the separated ligand is reacted with the exogenously supplied binding partner.

G. Polymerase Chain Reaction ("PCR") Thermal Cycling

One of the bottlenecks of the PCR technique is cooling time. The heating cycle is rapid; however, cooling is limited by convection. Even in biochip formats, in which DNA or to another target molecule is immobilized in an array on a microdevice, there is no "active" cooling process. However, certain embodiments of the invention can be used to overcome this bottleneck.

H. Purification, Separation, and Reaction Control

Focused sonic fields can be used to enhance separations. As noted elsewhere, sonic foci can be used to diminish or eliminate wall effects in fluid flow, which is an important element of many separation processes, such as chromatography including gas chromatography, size exclusion chromatography, ion exchange chromatography, and other known forms, including filed-flow fractionation. The ability to remotely modulate and/or reduce or eliminate the velocity and concentration gradients of a flowing stream is applicable in a wide variety of situations.

Sonic fields also can be used to minimize concentration polarization in membrane processes, including particle classification, filtration of fine particles and colloids, ultrafiltration, reverse osmosis, and similar processes. Concentration polarization is the result of the tendency of filtered material to be present at high concentration in a layer on the filter. This layer has a low fluid concentration and, thus, diminishes the rate of filtration as the filtered solution becomes more concentrated, or as the layer thickens. Therefore, the resistance of the fluid flows through the layer and filter is increased, which yields a reduced flow rate. This layer can be stirred remotely by focused sonic energy of low to moderate intensity. Flow rate, thus, can be enhanced without significant cost in energy or membrane life.

I. Further Uses for Remotely Actuated and Controlled Solution Mixing with Sonic Energy Control of sonic energy emission, sonic energy characteristics, and/or location of a target relative to sonic energy also can be used to pump and control the flow rate of liquids, especially in capillaries; enhance chemical reactions, such as enhancing second-order reaction rates; increase effective Reynolds number in fluid flow; and control the dispensing of semi-solid substances.

By focusing sonic energy and positioning it near a wall of a chamber or another discontinuity in a fluid path, many local differences in the distribution of materials within a sample and/or spatially-derived reaction barriers, particularly in reactive and flowing systems, can be reduced to the minimum delays required for microscopic diffusion. Put differently, enhanced mixing can be obtained in situations where imperfect mixing is common.

The controller 20 may include any suitable components to perform desired control, communication and/or other functions as described above. For example, the controller 20 may include one or more general purpose computers, a network of computers, one or more microprocessors, etc., for performing data processing functions, one or more memories for storing data and/or operating instructions (e.g., including volatile and/or non-volatile memories such as optical disks and disk drives, semiconductor memory, magnetic tape or disk memories, and so on), communication buses or other communication devices for wired or wireless communication (e.g., including various wires, switches, connectors, Ethernet communication devices, WLAN communication devices, and so on), software or other computer-executable instructions (e.g., including instructions for carrying out functions related to controlling the acoustic energy source 2, a pump, etc., as described above and other components), a power supply or other power source (such as a plug for mating with an electrical outlet, batteries, transformers, etc.), relays and/or other switching devices, mechanical linkages, one or more sensors or data input devices (such as a sensor to detect a temperature and/or presence of the material in a sample holder 10, a video camera or other imaging device to capture and analyze image information regarding the sample holder 10 or other components, position sensors to indicate positions of the acoustic transducer 2 and/or the vessel 10, and so on), user data input devices (such as buttons, dials, knobs, a keyboard, a touch screen or other), information display devices (such as an LCD display, indicator lights, a printer, etc.), and/or other components for providing desired input/output and control functions.

While aspects of the invention have been described with reference to various illustrative embodiments, such aspects are not limited to the embodiments described. Thus, it is evident that many alternatives, modifications, and variations of the embodiments described will be apparent to those skilled in the art. Accordingly, embodiments as set forth herein are intended to be illustrative, not limiting. Various changes may be made without departing from the spirit of aspects of the invention.

The invention claimed is:

1. A system for treating a material with acoustic energy, comprising:
   a coupling medium container that is closed and defines an internal volume, the coupling medium container having an outer surface arranged to rotate about an axis;
   an acoustic energy source arranged to emit acoustic energy from within the internal volume;
   a coupling medium located in the internal volume of the coupling medium container, the coupling medium being arranged to transmit acoustic energy from the acoustic energy source to a treatment area outside of the coupling medium container and near the outer surface; and
   a sample holder in contact with the outer surface of the coupling medium container, the sample holder including a tubular portion containing a sample including a liquid;
   wherein the coupling medium container outer surface is rotatable with movement of the sample holder relative to the treatment area, and the acoustic energy source is configured to transmit focused acoustic energy to the treatment area outside of the coupling medium container to form a focal zone of acoustic energy at the treatment area and to cause mixing of the liquid of the sample in the sample holder with the sample located at the treatment area.

2. The system of claim 1, wherein the outer surface is cylindrical and the axis passes through a center longitudinal axis of the cylindrical outer surface.

3. The system of claim 2, wherein the outer surface is rotatable with linear movement of the sample holder relative to the treatment area.

4. The system of claim 3, wherein the outer surface is rotatable with movement of the sample holder along a direction parallel to a tangent of the outer surface.

5. The system of claim 1, wherein the coupling medium is liquid.

6. The system of claim 1, wherein the acoustic energy source is arranged to emit acoustic energy having a frequency of about 100 kHz to 100 MHz.

7. The system of claim 1, wherein the coupling medium container is completely filled with the coupling medium.

8. The system of claim 1, wherein the acoustic energy source is located inside the coupling medium container and is immersed in the coupling medium.

9. The system of claim 1, further comprising a heat exchanger arranged to exchange heat with the coupling medium.

10. The system of claim 1, further comprising a roller positioned above the treatment area and arranged to rotate about a roller axis, the roller arranged to contact a sample holder positioned between the coupling medium container and the roller and urge the sample holder into contact with the coupling medium container.

11. The system of claim 10, wherein the roller and the outer surface are rotatable to move a sample holder relative to the treatment area.

12. The system of claim 11, wherein the roller and the outer surface are rotatable to move a sample holder in a linear direction relative to the treatment area.

13. The system of claim 1, wherein the outer surface includes a resilient material to contact the sample holder.

14. The system of claim 1, wherein the acoustic energy source includes a piezoelectric transducer to emit acoustic energy.

15. The system of claim 1, wherein the focal zone is outside of the coupling medium container.

* * * * *

UNITED STATES PATENT AND TRADEMARK OFFICE
CERTIFICATE OF CORRECTION

PATENT NO. : 11,092,521 B2
APPLICATION NO. : 14/463730
DATED : August 17, 2021
INVENTOR(S) : Laugharn, Jr. et al.

Page 1 of 1

It is certified that error appears in the above-identified patent and that said Letters Patent is hereby corrected as shown below:

In the Specification

At Column 1, Line 63, "and/or to biological" should read -- and/or biological --

At Column 3, Line 28, "holder is to exposed" should read -- holder is exposed --

At Column 10, Line 44, "including to sonic welding" should read -- including sonic welding --

At Column 15, Line 56, "induce the stiffing" should read -- induce the stirring --

At Column 23, Line 21, "DNA or to another" should read -- DNA or another --

Signed and Sealed this
Fourteenth Day of September, 2021

Drew Hirshfeld
*Performing the Functions and Duties of the*
*Under Secretary of Commerce for Intellectual Property and*
*Director of the United States Patent and Trademark Office*